United States Patent
Habermeyer et al.

[11] Patent Number: 5,575,801
[45] Date of Patent: Nov. 19, 1996

[54] METHOD AND APPARATUS FOR ARTHROSCOPIC ROTATOR CUFF REPAIR

[75] Inventors: Peter Habermeyer, Stuttgart, Germany; Reinhold Schmieding, Naples, Fla.

[73] Assignee: Arthrex, Inc., Naples, Fla.

[21] Appl. No.: 288,228

[22] Filed: Aug. 26, 1994

Related U.S. Application Data

[63] Continuation-in-part of Ser. No. 197,829, Feb. 17, 1994, Pat. No. 5,466,243.

[51] Int. Cl.$^6$ ..................................................... A61B 17/00
[52] U.S. Cl. ........................ 606/148; 606/207; 606/232; 606/96
[58] Field of Search ...................... 606/205–208, 606/148, 232, 151, 139, 147, 116, 117, 96, 97, 98

[56] References Cited

U.S. PATENT DOCUMENTS

| | | | |
|---|---|---|---|
| 2,665,692 | 1/1954 | L'Esperance | 606/148 |
| 4,632,100 | 12/1986 | Somers et al. | 606/73 |
| 4,738,255 | 4/1988 | Goble et al. | 606/86 |
| 4,898,156 | 2/1990 | Gatturna et al. | 606/72 |
| 4,899,743 | 2/1990 | Nicholson et al. | 606/139 |
| 4,920,958 | 5/1990 | Walt et al. | 606/96 |
| 4,923,461 | 5/1990 | Caspari et al. | 606/146 |
| 5,176,691 | 1/1993 | Pierce | 606/148 |
| 5,209,747 | 5/1993 | Knoepfler | 606/16 |
| 5,211,650 | 5/1993 | Noda | 606/139 |
| 5,217,468 | 6/1993 | Clement | 606/127 |
| 5,222,962 | 6/1993 | Burkhart | 606/148 |
| 5,250,055 | 10/1993 | Moore et al. | 606/148 |
| 5,257,637 | 11/1993 | El Gazayerli | 606/205 |
| 5,269,786 | 12/1993 | Morgan | 606/96 |
| 5,281,230 | 1/1994 | Heidmueller | 606/127 |
| 5,286,255 | 2/1994 | Weber | 604/22 |
| 5,304,203 | 4/1994 | El-Mallawany et al. | 606/207 |
| 5,312,432 | 5/1994 | Pingleton et al. | 606/205 |
| 5,318,579 | 6/1994 | Chow | 606/148 |
| 5,370,662 | 12/1994 | Stone et al. | 606/232 |
| 5,372,604 | 12/1994 | Trott | 606/232 |
| 5,382,258 | 1/1995 | Chow | 606/205 |
| 5,409,494 | 4/1995 | Morgan | 606/96 |

OTHER PUBLICATIONS

S. J. Snyder, M. D., "The Revo Rotator Cuff Fixation System," Linvatec Corporation, 1993.

*Primary Examiner*—Michael Powell Buiz
*Assistant Examiner*—Jeffrey A. Schmidt
*Attorney, Agent, or Firm*—Ostrolenk, Faber, Gerb & Soffen, LLP

[57] ABSTRACT

A method and apparatus for arthroscopic reattachment of torn tissue to a bone at a surgical repair site using at least one suture anchor and a tissue grasper. The torn tissue is grasped with jaws of the tissue grasper. The jaws include a top and bottom jaw. The upper jaw has an aperture, and the bottom jaw has a U-shaped slot. The aperture and slot are aligned with each other when the jaws are closed. A threaded suture anchor is inserted through the aligned aperture and slot in the jaws of the grasper, the grasped tissue, and into the bone in a single drilling step. An outrigger located on the barrel of the grasper is adapted to receive a drill and align the threaded suture anchor such that the suture anchor is automatically aligned with the aperture and slot of the jaws of the grasper at the repair site. After insertion of the suture anchor the grasper is removed from the repair site. The upper jaw of the grasper with the aperture simultaneously retrieves suture attached to the inserted anchor as the grasper is removed.

20 Claims, 6 Drawing Sheets

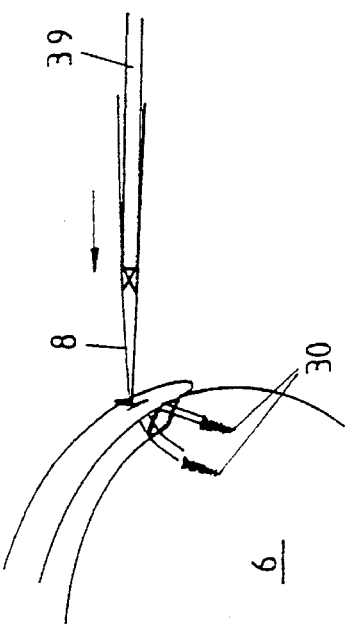
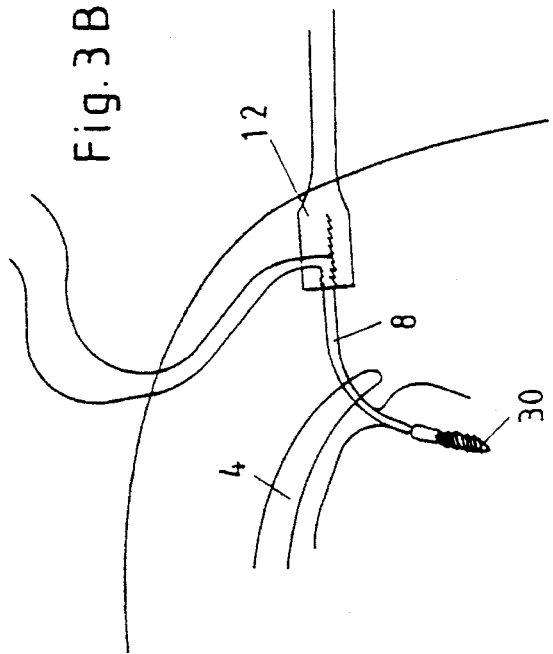
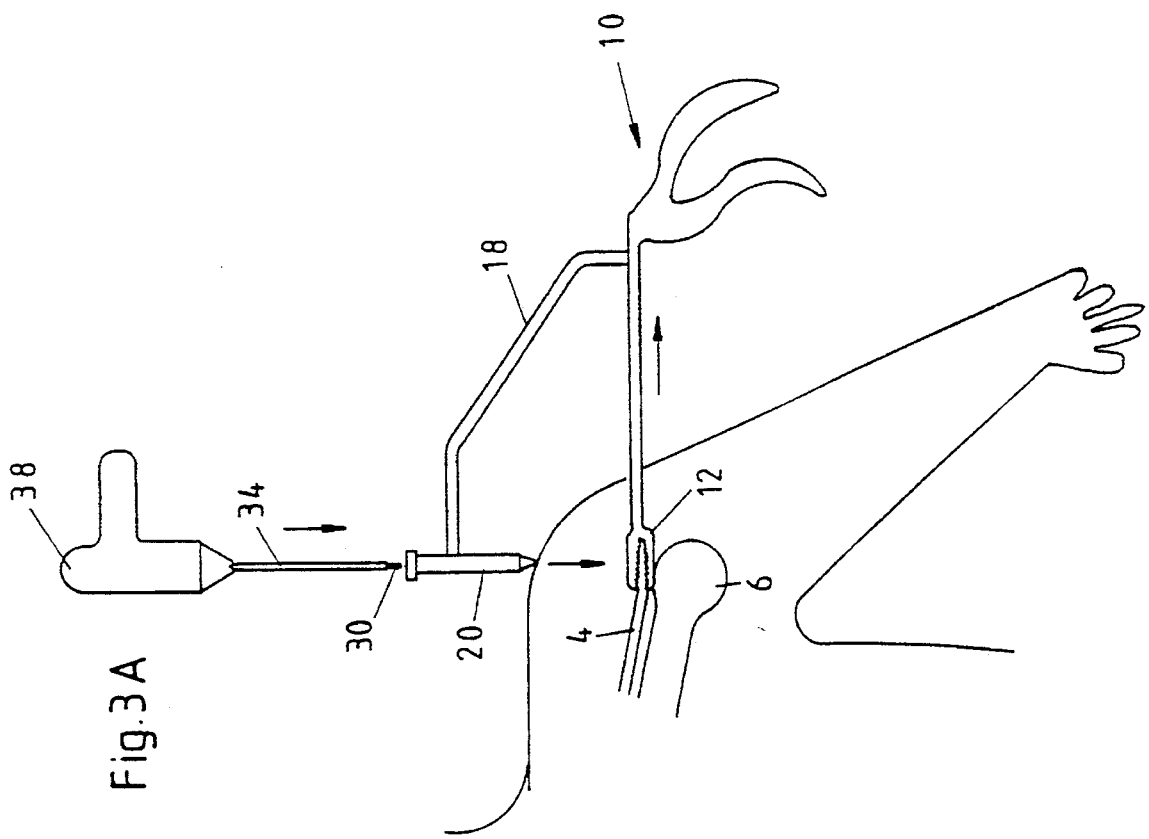

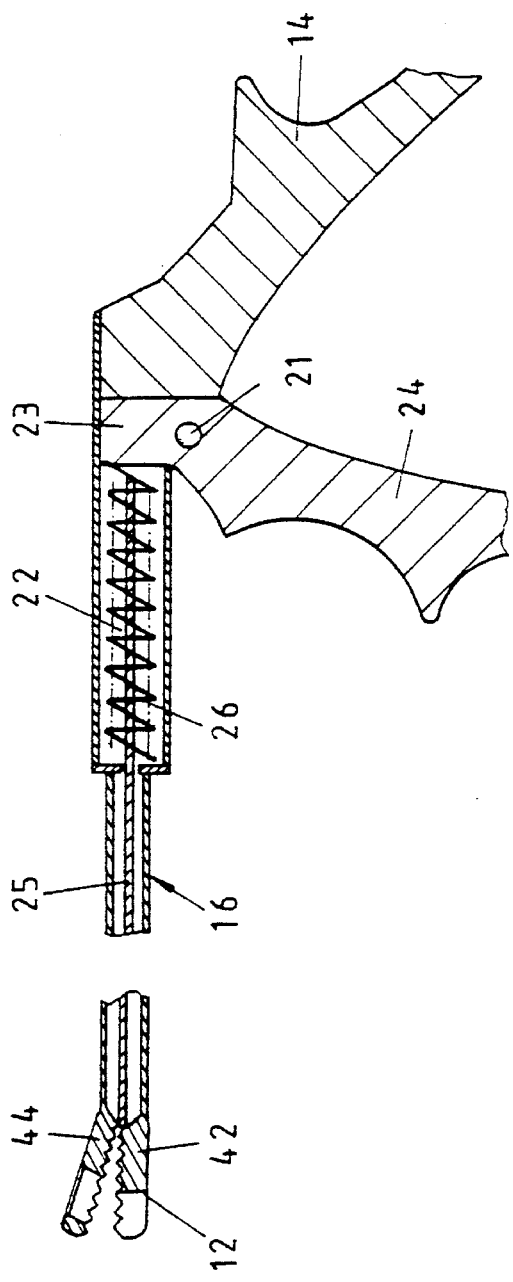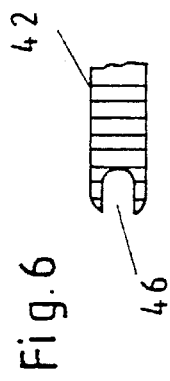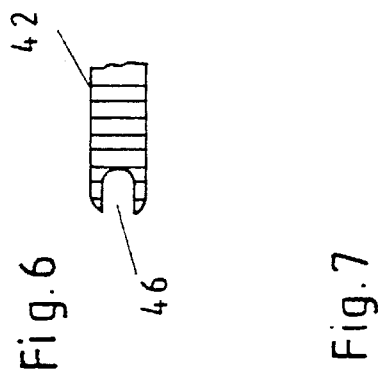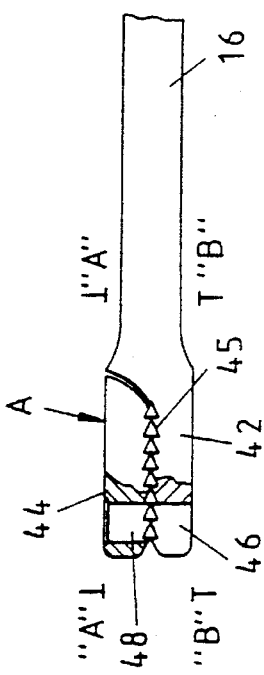

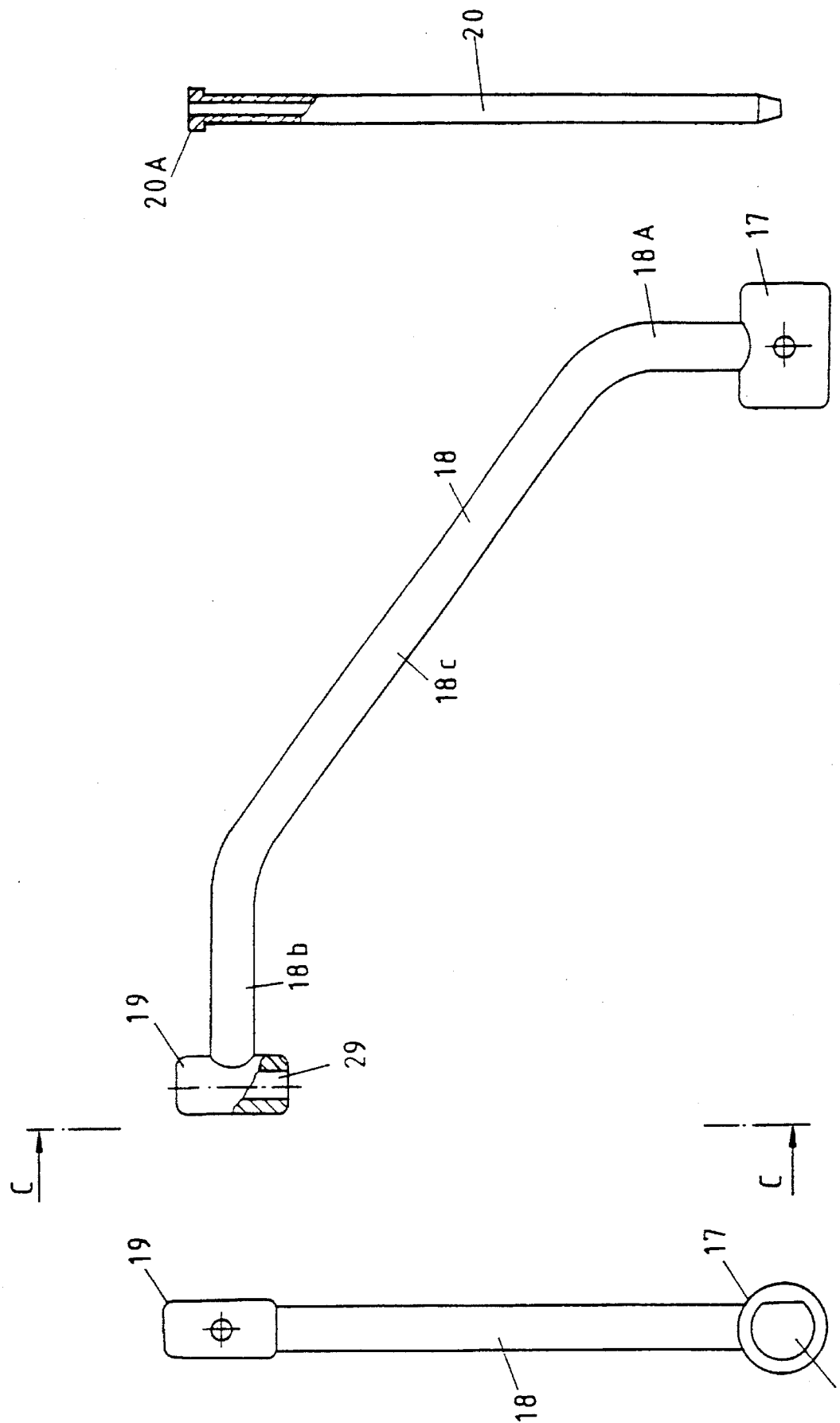

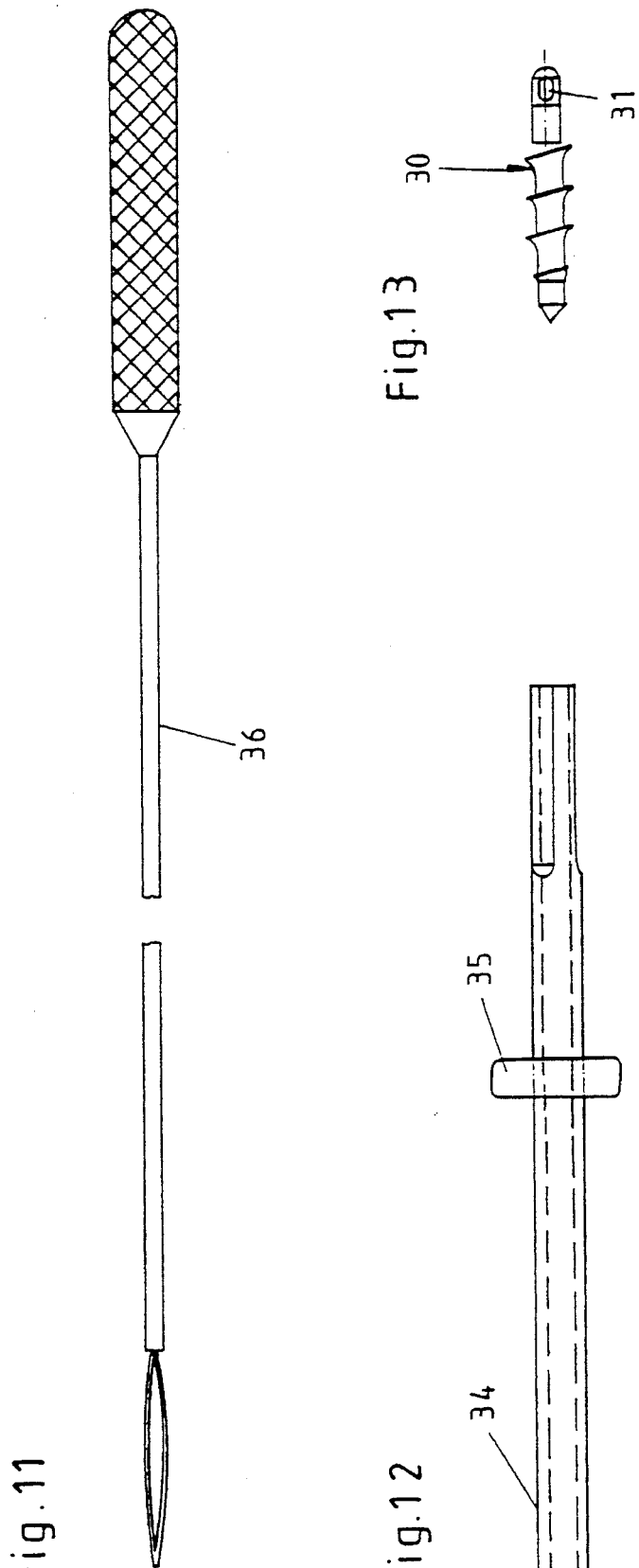

METHOD AND APPARATUS FOR ARTHROSCOPIC ROTATOR CUFF REPAIR

This is a continuation-in-part of application Ser. No. 08/197,829, filed Feb. 17, 1994, now U.S. Pat. No. 5,466,243 the disclosure of which being herein incorporated by reference.

BACKGROUND OF THE INVENTION

1. Field of the Invention

The present invention relates to a method and apparatus for arthroscopic repair of torn tissue, and more particularly to a method and device for arthroscopic repair of a torn rotator cuff.

2. Description of the Related Art

As shown in FIG. 1, when a tear 2 occurs in the rotator cuff 4 of the shoulder, it is necessary to reattach the torn tendon to the bone of the humeral head 6.

Various repair methods are known. However, the known reattachment procedures are lengthy and complicated. In a surgical technique as described by Stephen J. Snyder, MD, Southern California Orthopedic Institute in "The Revo Rotator Cuff Fixation System", Linvatec Corp. (1993), screws pre-threaded with suture are first drilled into the bone and the suture threaded through each screw is retrieved from the repair site using a hook. A suture punch is used to puncture the torn cuff, and a shuttle is passed through the cuff and retrieved from an anterior cannula using a grasper instrument. An eyelet in the shuttle is loaded with a free end of the suture passing through one of the screws, and the shuttle is pulled through the cuff and out the anterior cannula using the grasper. This suturing procedure is repeated with the second free end of suture passing through the screw, after which the pair of suture strands is withdrawn from the lateral cannula. The above procedure is repeated until all of the suture strands from the screws are passed though the tear. The suture strands are then knotted and tied together to secure the reattached rotator cuff.

The above surgical technique is an "open" technique and, as with most open techniques, morbidity of the repair site can occur. Another disadvantage with the above-described technique is that separate grasping and puncturing instruments are required.

As in the above technique, it is known to grasp tissue using forceps during suturing. See, e.g., U.S. Pat. Nos. 2,665,692 to L'Esperance and 5,304,203 to El-Mallawany et al. The forceps of U.S. Pat. No. 2,665,692 also include jaws 13 and 14 having openings which allow the surgeon to pass a needle therethrough. However, the forceps of this patent are not designed for arthroscopic surgical procedures.

All of the prior art techniques and devices discussed above require separate instruments to grasp the tissue to be repaired and to retrieve the suture from the arthroscopic surgery site. Thus, up to now, it has been necessary to use numerous different surgical devices in the confines of a very small area.

SUMMARY OF THE INVENTION

The present invention provides a method and device for the arthroscopic reattachment of torn tissue which overcomes the above-noted deficiencies of the prior art.

In the method of the present invention, torn tissue is reattached to bone using at least one suture anchor and a tissue grasper. The tissue grasper grasps the torn tissue with jaws. A first threaded suture anchor is inserted through the jaws of the grasper, the grasped tissue, and into the bone in a single drilling step. As the grasper is removed from the repair site, the grasper jaws simultaneously retrieve the suture from the repair site.

The tissue grasper of the present invention includes an elongated barrel having first and second opposed ends, the first end being insertable into a patient to the repair site. A pair of pivotable jaws are located on the first end of the barrel for grasping the torn tissue. The jaws include a top and a bottom jaw. The top jaw has an aperture, and the bottom jaw includes a U-shaped slot. The aperture and slot are aligned with each other when the jaws are closed.

A drilling guide outrigger located on the barrel is adapted to receive and align the threaded suture anchor, such that the suture anchor is automatically aligned with the aperture and slot of the grasper jaws at the repair site.

An important advantage of the method and apparatus of the present invention is that the grasper allows the surgeon to grasp the tissue, insert the suture through the grasped tissue, and drill the suture anchor into the bone in a single drilling step. Thus, in accordance with the present invention, it is not necessary for the surgeon to thread a suture needle, reintroduce the threaded needle back into the repair site, and stitch the torn tissue. Thus, surgery time is significantly reduced.

Another significant advantage of the present invention is that the grasper automatically retrieves the suture from the repair site as the grasper itself is removed. Therefore, a separate instrument for retrieving the suture is not required.

Other features and advantages of the present invention will become apparent from the following description of the invention which refers to the accompanying drawings.

BRIEF DESCRIPTION OF THE DRAWINGS

FIGS. 3a–3c illustrate the surgical method of the present invention.

FIG. 4 is a cross-section of the grasper of the present invention.

FIG. 5 is an enlarged cross-section of the jaws of the grasper.

FIG. 6 is a bottom view of the jaws taken along line A—A of FIG. 5.

FIG. 7 is a top view of the jaws taken along line B—B of FIG. 5.

FIG. 8 is a side, partial cross-sectional view of the outrigger guide of the present invention.

FIG. 9 is a front view of the outrigger taken along line C—C of FIG. 8.

FIG. 10 is a partial cross-sectional view of a cannula received in the outrigger.

FIG. 11 illustrates a suture threading device used with the apparatus and method of the present invention.

FIG. 12 illustrates a device driver used with the apparatus and method of the present invention.

FIG. 13 illustrates a suture anchor used with the apparatus and method of the present invention.

DETAILED DESCRIPTION OF THE PREFERRED EMBODIMENT

The present invention relates to a method and apparatus for the arthroscopic repair of torn tissue and bone at a surgical repair site using a tissue grasper. Although the present invention is described primarily in conjunction with the repair of a torn rotator cuff, the apparatus and method can be also be used for arthroscopic Bankart shoulder repair, as well as elbow, knee, ankle and hip surgery, and other surgical techniques.

Figure 1:
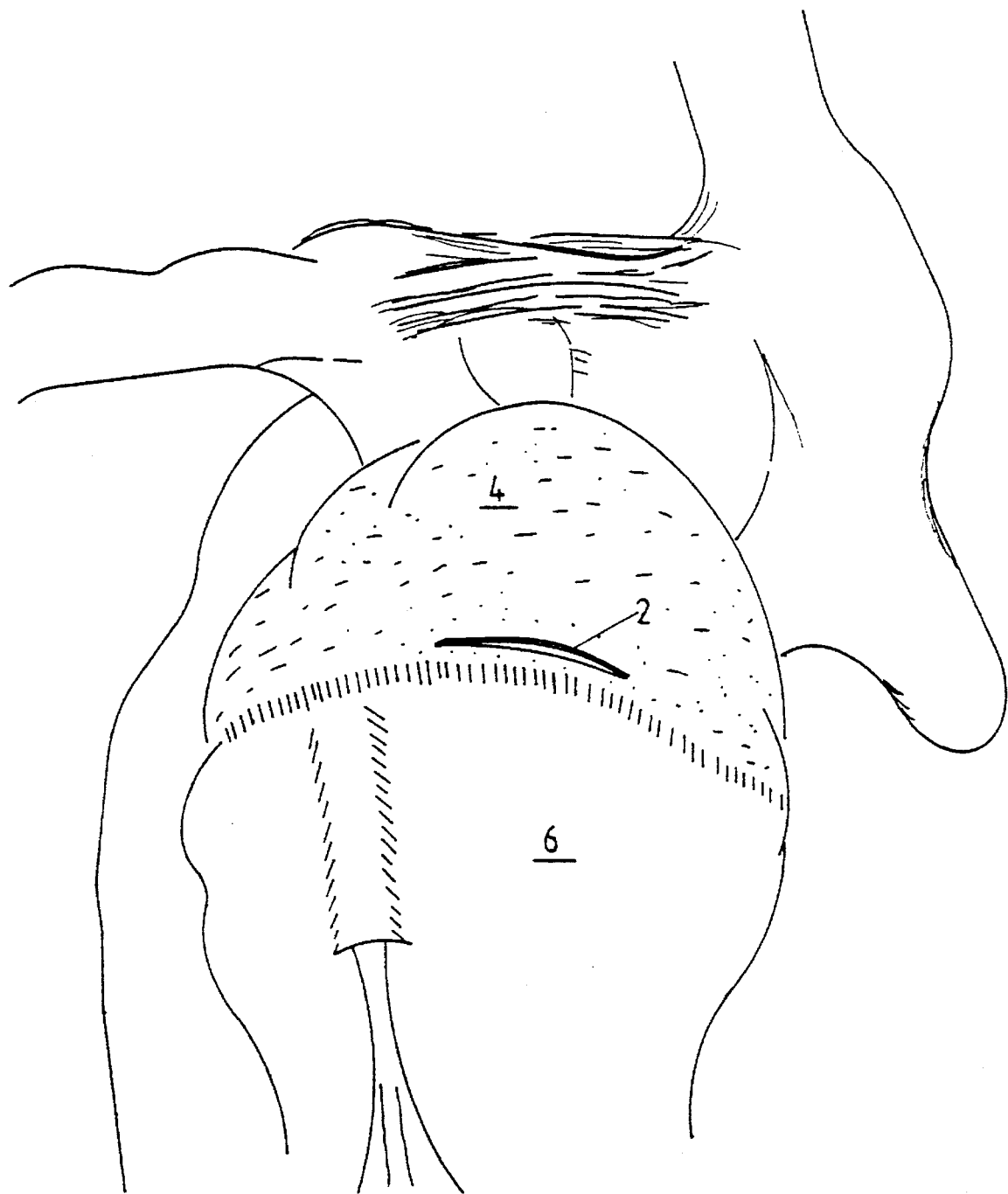
FIG. 1 illustrates a torn rotator cuff.
Figure 2:
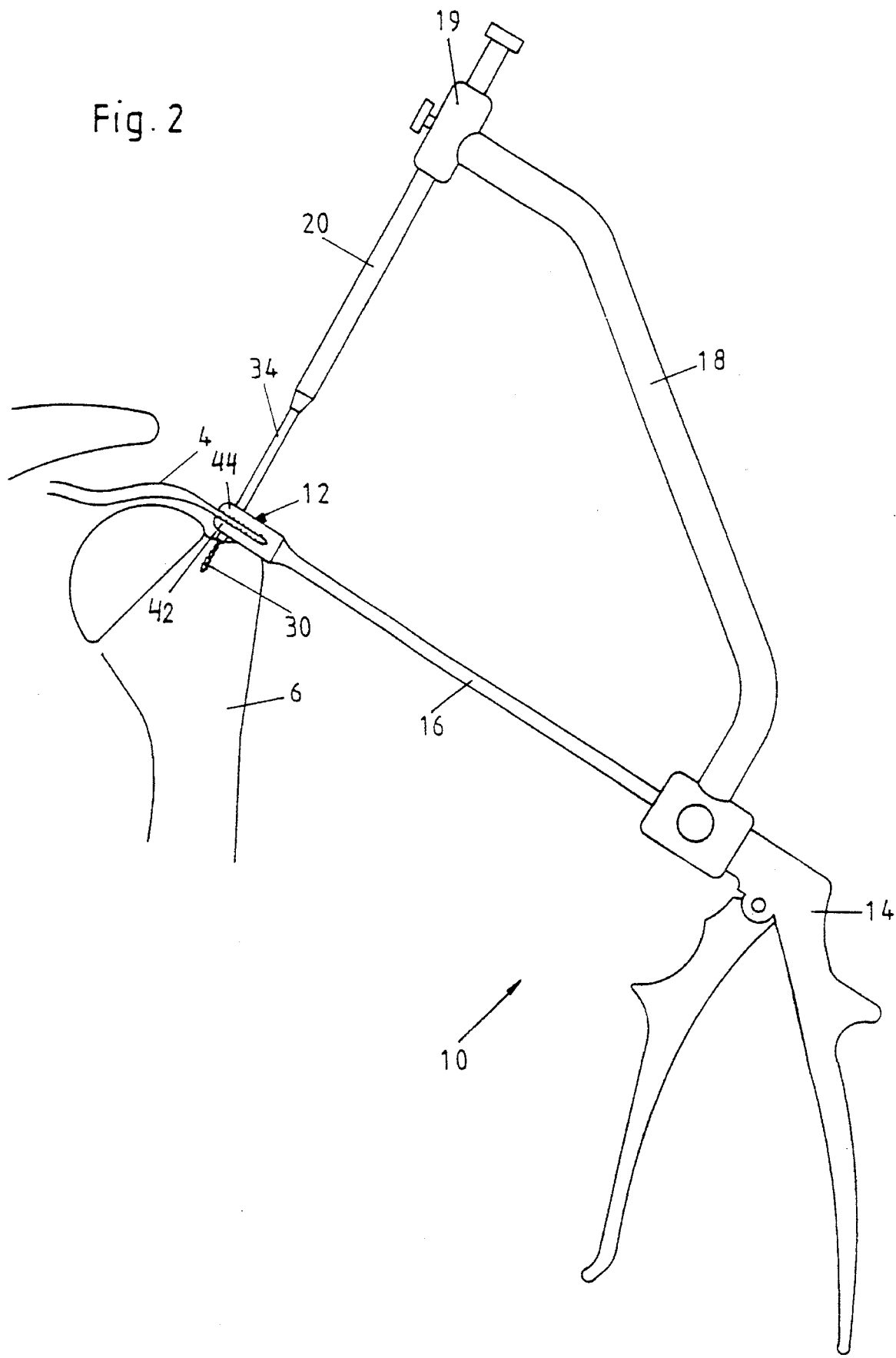
FIG. 2 is a perspective view of the grasper of the present invention, showing the rotator cuff being held by the jaws of the grasper.

As shown in FIG. 2, in accordance with the present invention, a grasper 10 is provided with pivotable jaws 12 for grasping a torn rotator cuff 4. The jaws 12 are disposed at the distal end of a hollow barrel 16. A handpiece 14 is located at the proximal end of barrel 16. An outrigger drill guide 18 extends over and is supported on barrel 16.

Referring to FIGS. 5–7, jaws 12, disposed at the distal end of barrel 16, include a lower stationary jaw 42 and an upper moveable jaw 44. Both jaws 42 and 44 include teeth 45 to grip the tissue.

As shown in FIG. 6, lower stationary jaw 42 is provided with a U-shaped slot 46, while moveable jaw 44 is provided with a completely enclosed aperture 48, see FIG. 7. When the jaws are in a closed position, as shown in FIG. 5, the slot 46 and aperture 48 are aligned to allow passage of a suture anchor therethrough. As discussed in further detail below, when grasper 10 is removed from the repair site after the anchor has been embedded, suture passing through jaws 12 is caught in aperture 48 and simultaneously removed from the repair site.

As shown in FIGS. 8–10, outrigger 18 has a lower end 17 and a upper end 19. Lower end 17 includes a hollow portion 27 through which barrel 16 extends. Upper end 19 is provided with a cannulation 29 for receiving cannula 20. Cannula 20 in turn receives a device driver 34 (FIGS. 2, 12) loaded with a threaded suture anchor 30 to be embedded within the bone 6. The suture anchor 30, shown in detail in FIG. 13, is a self-tapping screw; therefore, no predrilling of pilot bores in the bone is necessary.

Outrigger 18 has a first leg 18A which extends vertically from lower end 17, a second leg 18B extending horizontally from upper end 19, and a connecting leg 18C extending between legs 18A and 18B. As discussed in further detail below, outrigger 18 is configured to automatically align the cannula 20, and thus driver 34 and suture anchor 30 passing therethrough, with the aperture 48 and slot 46 in the jaws.

Device driver 34 is provided with an adjustable depth stop 35 (see FIG. 12) to allow the surgeon to control the depth of implantation of suture anchor 30. As shown in FIG. 10, cannula 20 has a lip 20A at its proximal end through which driver 34 is received. Depth stop 35 engages lip 20A to prevent further advancement of the anchor.

In the method of the present invention, the grasper 10 is inserted into a portal in the shoulder. The portal is opened by first making an incision in the skin then inserting a cannula (not shown) through the incision. The distal end of hollow barrel 16 is inserted through the cannula until the jaws 12 reach the torn rotator cuff tissue. After the instrument is in place, grasper 10 is operated by manipulating handpiece 14 such that the torn tissue 4 is grasped by jaws 12.

Next, cannula 20 is slid downwards until the tip is flush with the skin of the patient as shown in FIG. 3A. As stated previously, outrigger 18 is designed such that the cannula 20 is automatically aligned with slot 46 and corresponding aperture 48 in the lower/upper jaws 42, 44 of the grasper.

Next, a suture anchor 30 is pre-threaded with the proper size suture inserted through eye 31. A threading device 36, as shown in FIG. 11, can be used to facilitate threading of the suture through device driver 34.

The eyelet end of the now threaded suture anchor is then seated in device driver 34. The device driver 34, with the suture anchor 30 at its distal end, is inserted through cannula 20 into an incision in the patient. A power drill is attached to driver 34 for rotating the driver and the suture anchor secured at the distal end thereof. The suture anchor 30 is advanced through aperture 48 in upper jaw 44 and slot 46 in lower jaw 42 and drilled through the grasped tissue and into the bone in a single drilling step, see FIG. 2.

Once suture anchor 30 is drilled into the bone, driver 34 is removed. Referring to FIG. 3B, grasper 10 is removed from the repair site and the threaded suture anchor is left in place. As grasper 10 is retracted, the suture 8 passing through aperture 48 in upper jaw 44 is simultaneously removed from the repair site.

Ordinarily, the entire procedure is repeated to insert additional threaded suture anchors. As shown in FIGS. 3B and 3C, the double stranded suture 8 extends from anchors 30 and through the torn rotator cuff tissue 4. Mattress stitches are made by tying one strand of suture from one of the anchors to the other anchor and vice versa. The knots may be tied and advanced into the shoulder using a knot-pusher 39, as described in U.S. Pat. No. 5,176,691.

The details of the grasper 10 of the present invention will now be described.

The handpiece 14 of grasper 10 includes a trigger 24 pivotally connected to the handpiece by pivot pin 21. As shown in FIG. 4, trigger 24 includes an extension 23 which projects into the hollow portion 22 of the handpiece. Barrel 16 is secured to the handpiece at one end. In operation, the distal end of the grasper is positioned at the repair site against the tissue to be grasped. Moveable jaw 44 is advanced toward stationary jaw 42 by squeezing trigger 24. As trigger 24 moves inward by pivoting about pivot pin 21, extension 23 is urged against rod 25, advancing rod 25 forward toward the distal end of barrel 16 against the force of spring 26. When rod 25 is advanced forward, moveable jaw 44 pivots toward stationary jaw 42 to close the jaws. Once the appropriate section of tissue is isolated and grasped by jaws 42, 44, the trigger 24 may be locked in its closed position, using a latch mechanism (not shown).

Although the present invention has been described in relation to particular embodiments thereof, many other variations and modifications and other uses will become apparent to those skilled in the art. It is preferred, therefore, that the present invention be limited not by the specific disclosure herein, but only by the appended claims.

What is claimed is:

1. An apparatus for arthroscopic reattachment of torn tissue to a bone at a surgical repair site within a patient using a suture anchor threaded with suture, comprising:

an elongated barrel having proximal and distal opposed ends, the distal end being insertable into the patient to the repair site;

grasping means located on the distal end of the barrel for grasping the torn tissue at the repair site within the patient;

means disposed on the grasping means for receiving the threaded suture anchor at the repair site within the patient and for retrieving the suture, the suture remaining attached to the threaded suture anchor at the repair site within the patient, when the distal end of the barrel is removed from the repair site; and means for aligning a drill including a receptacle having a longitudinal axis, the longitudinal axis being aligned with the means for receiving the threaded suture anchor, wherein the threaded suture anchor is inserted through the means for receiving the threaded suture anchor, the grasped tissue, and into the bone in a single drilling step.

2. The apparatus of claim 1, wherein the grasping means comprises a pair of pivotable jaws.

3. The apparatus of claim 2, wherein the jaws include a top and bottom jaw, the receiving means comprising an aperture in the top jaw and a slot in the bottom jaw, the aperture and slot being aligned with each other when the jaws are closed, and wherein the threaded suture anchor is inserted through the aligned aperture and slot, the torn tissue and into the bone.

4. The apparatus of claim 3, wherein the slot in the bottom jaw is U-shaped.

5. The apparatus of claim 3, further comprising means disposed on the elongated barrel for guiding and aligning the suture anchor with the aperture in the top jaw and the slot in the bottom jaw.

6. The apparatus of claim 5, wherein the guiding means comprises an outrigger located on the barrel adapted to receive a drill such that the threaded suture anchor can be automatically aligned with the aperture and slot disposed on the grasping means.

7. The apparatus of claim 6, wherein the outrigger has a lower end and an upper end, the lower end being hollow to receive the barrel of the grasper and the upper end having a cannulation for receiving a cannula through which the threaded suture anchor is advanced toward the repair site.

8. The apparatus of claim 7, wherein the outrigger has a first leg extending from the lower end, a second leg extending from the upper end, and a connecting leg linking the first and second legs.

9. The apparatus of claim 3, further comprising:
a hollow handpiece having opposed front and back ends, the proximal end of the elongated barrel being secured to the front end of the handpiece, wherein the bottom jaw is attached to the barrel at the distal end thereof; and
an elongated rod movably disposed within the barrel, the rod being attached at a distal end thereof to the top jaw.

10. The apparatus of claim 9, wherein the handpiece includes a pistol grip disposed on the handpiece, and a trigger pivotally connected to the handpiece.

11. The apparatus of claim 10, wherein the trigger comprises an extension, and the trigger extension extends into the hollow handpiece and cooperates with the rod to move the rod in the barrel when the trigger pivots with respect to the handpiece.

12. The apparatus of claim 11, further comprising a spring disposed on the rod between the trigger extension and the barrel, and the trigger and the top jaw are urged by the spring into a normally open position.

13. An apparatus for arthroscopic reattachment of torn tissue to a bone at a surgical repair site within a patient using a suture anchor threaded with suture, comprising:
an elongated barrel having a central axis and proximal and distal opposed ends, the distal end being insertable within the patient to the repair site;
a pair of closeable grasping jaws located on the distal end of the barrel for grasping the torn tissue at the repair site within the patient, each of the grasping jaws having an opening, the openings aligning when the grasping jaws are in a closed position; and
an outrigger disposed on the barrel having a receptacle for receiving a drill, the receptacle having a longitudinal axis aligned with the openings in the grasping jaws such that the threaded suture anchor can be disposed on the drill for insertion within the patient whereby the suture anchor is automatically aligned to pass through the openings aligned when the jaws of the grasping means are closed, the torn tissue, and into the bone for installation at the repair site.

14. The apparatus of claim 13, wherein at least one of the openings on the jaws is enclosed for capturing the suture threaded on the suture anchor installed into the bone at the repair site, and for retrieving the suture, the suture remaining attached to the suture anchor at the repair site within the patient, when the distal end of the barrel is removed from the repair site.

15. The apparatus of claim 13, wherein the outrigger includes a cannula for disposed on a distal end thereof, the cannula receiving the drill and aligning the drill with the openings aligned with the jaws in the closed position.

16. The apparatus of claim 13, wherein the outrigger is for aligning a central axis of the drill at substantially a right angle with respect to the central axis of the elongated barrel.

17. A method for arthroscopic reattachment of torn tissue to a bone at a surgical repair site using at least one suture anchor and a tissue grasper provided with jaws, comprising the steps of:
grasping the torn tissue with the jaws of the tissue grasper;
inserting a first suture anchor threaded with suture through the jaws of the tissue grasper, the grasped tissue, and into the bone in a single drilling step; and
removing the tissue grasper from the repair site, the jaws of the tissue grasper simultaneously retrieving the suture threaded into the inserted anchor as the grasper is removed from the repair site.

18. The method of claim 17, wherein the jaws include a top jaw and a bottom jaw, the top jaw having an aperture and the bottom jaw having a U-shaped slot, the aperture and slot being aligned with each other when the jaws are closed, and wherein the step of inserting comprises inserting the suture anchor through the aligned aperture and slot of the jaws.

19. The method of claim 18, wherein the step of inserting further comprises the steps of:
coupling the suture anchor to a distal end of a device driver;
inserting the suture anchor and device driver through an outrigger disposed on the grasper, the outrigger automatically aligning the suture anchor with the aligned jaw aperture and U-shaped slot;
attaching a drill to a proximal end of the device driver; and
drilling the threaded suture anchor through the aperture in the top jaw, the grasped tissue, the slot in the bottom jaw and into the bone.

20. The method of claim 19, further comprising the step of inserting a second threaded suture anchor and tying the suture from the first and second suture anchors together over the torn tissue to secure the tissue to the bone.

* * * * *